US00PP32658P2

(12) United States Plant Patent
de Gruyter

(10) Patent No.: US PP32,658 P2
(45) Date of Patent: Dec. 15, 2020

(54) ***SALVIA* PLANT NAMED 'GRUSALRP'**

(50) Latin Name: ***Salvia* x *sylvestris***
Varietal Denomination: GRUSALRP

(71) Applicant: André de Gruyter B.V., Rockanje (NL)

(72) Inventor: Andre de Gruyter, Rockanje (NL)

(73) Assignee: André de Gruyter B.V., Rockanje (NL)

( * ) Notice: Subject to any disclaimer, the term of this patent is extended or adjusted under 35 U.S.C. 154(b) by 0 days.

(21) Appl. No.: 16/873,494

(22) Filed: Apr. 21, 2020

(51) Int. Cl.
*A01H 6/50* (2018.01)
*A01H 5/02* (2018.01)

(52) U.S. Cl.
USPC ..... Plt./475

(58) Field of Classification Search
USPC ..... Plt./475
See application file for complete search history.

(56) References Cited

PUBLICATIONS

PLUTO Plant Variety Database Sep. 19, 2020. p. 1.*

* cited by examiner

*Primary Examiner* — Annette H Para
(74) *Attorney, Agent, or Firm* — Samuel R. McCoy, Jr.

(57) ABSTRACT

'GRUSALRP' is a new and distinctive *Salvia* plant which is characterized by a broad upright growth habit, a broad inverted triangular plant form, large dark green foliage, an abundance of dark violet flowers borne on long terminal inflorescences that sit above the foliage, and plants bearing a large number of inflorescences at once. The new variety propagates successfully by stem cuttings and has shown to be uniform and stable in the resulting generations from asexual propagation.

3 Drawing Sheets

Latin name of the genus and species: The Latin name of the genus and species of the novel variety disclosed herein is *Salvia* x *sylvestris*.

Variety denomination: The inventive variety of *Salvia* disclosed herein has been given the variety denomination 'GRUSALRP'.

BACKGROUND OF THE INVENTION

Parentage: 'GRUSALRP' is a naturally occurring, whole-plant mutation of *Salvia* x *sylvestris* 'Rianne' (Community Plant Variety Rights grant number 41746) which was discovered at a commercial nursery in Rockanje, the Netherlands in May of 2019. The mutation was noted for its abundance of tall inflorescence bearing an abundance of dark violet flowers. The mutation was isolated for further evaluation in order to confirm the distinctness and stability of the characteristics first observed. Upon confirmation of distinctness and stability, 'GRUSALRP' was selected for commercialization.

Asexual Reproduction: Asexual reproduction of 'GRUSALRP' was first accomplished in autumn of 2019 by rooting softwood stem cuttings at a commercial greenhouse in Rockanje, the Netherlands. Two successive generations have shown that the unique features of the instant cultivar are stable and reproduce true to type.

SUMMARY OF THE INVENTION

The cultivar 'GRUSALRP' has not been observed under all possible environmental conditions and the phenotype may vary somewhat with variations in the instant environment such as temperature, day length, and light intensity, without, however, any variance in genotype. The following traits have been repeatedly observed and represent the distinguishing characteristics of the new *Salvia* plant, 'GRUSALRP'.

1. *Salvia* 'GRUSALRP' exhibits a broad, upright growth habit with a broad, inverted triangular plant profile; and
2. *Salvia* 'GRUSALRP' exhibits large, dark green foliage; and
3. *Salvia* 'GRUSALRP' exhibits an abundance of relatively large, dark violet labiate flowers borne on long, terminal verticillaster inflorescences that sit above the foliage; and
4. *Salvia* 'GRUSALRP' exhibits a floriferous flowering habit with plants bearing a large number of inflorescences at once.

BOTANICAL DESCRIPTION OF THE PLANT

Figure 1:
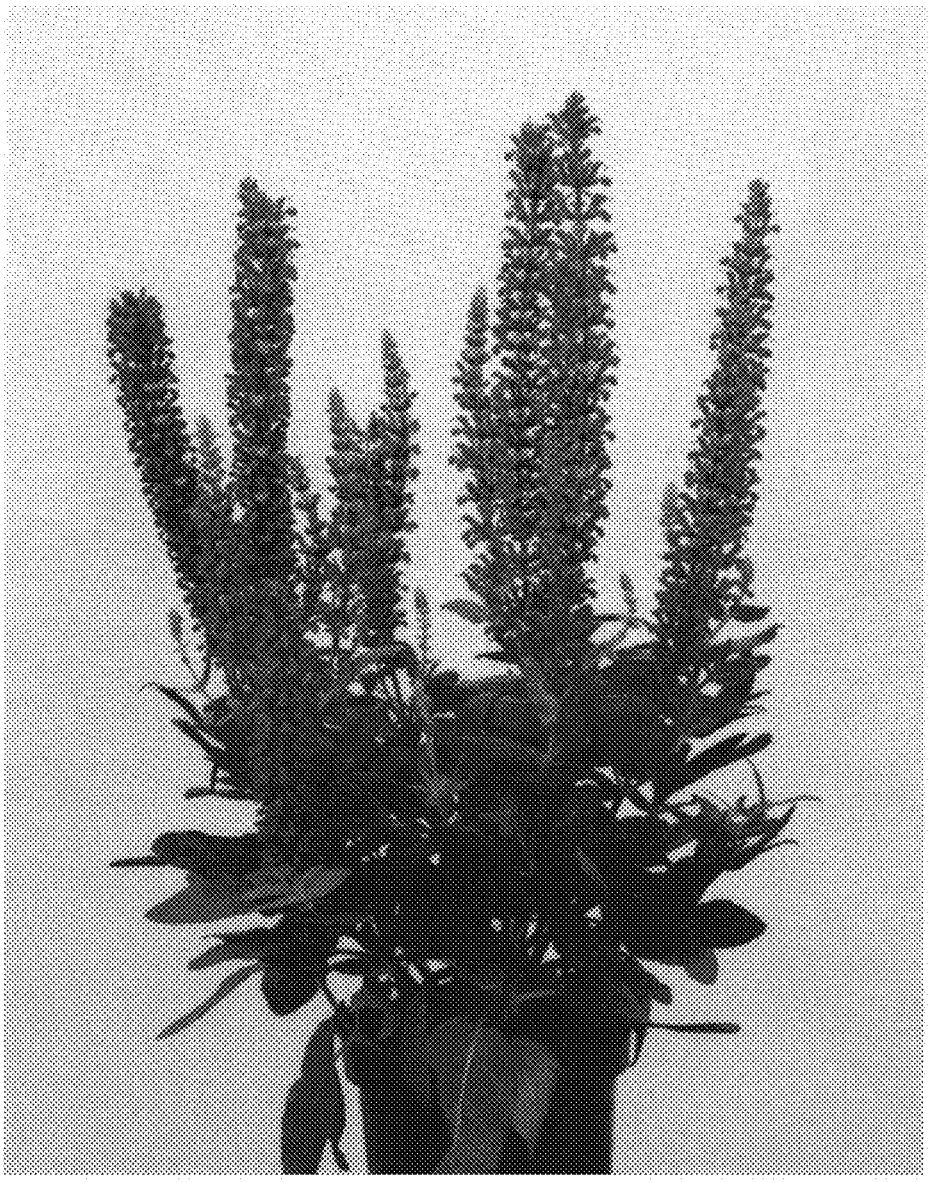
FIG. 1 shows, as nearly true as it is reasonably possible to make the same in color illustrations of this type, an exemplary 'GRUSALRP' plant at approximately 3 months old, potted into an 11 cm nursery pot, grown in a greenhouse in Rockajne, the Netherlands.
Figure 2:
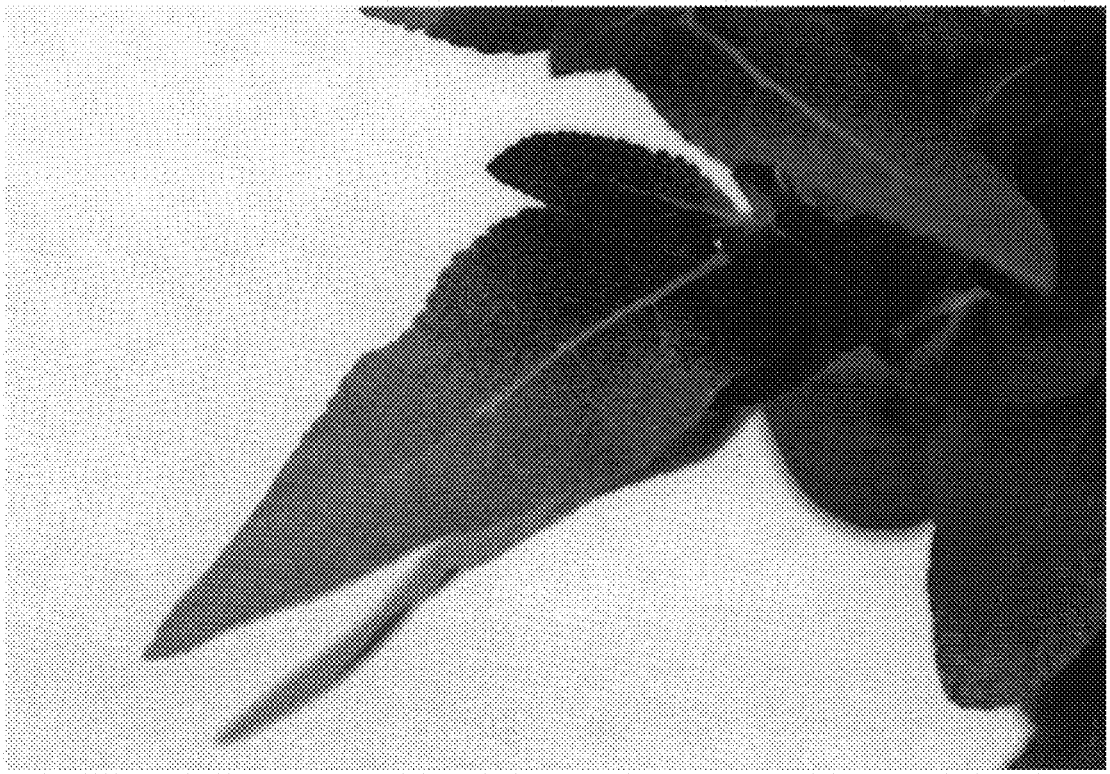
FIG. 2 shows, as nearly true as it is reasonably possible to make the same in color illustrations of this type, the typical foliage of 'GRUSALRP'.
Figure 3:
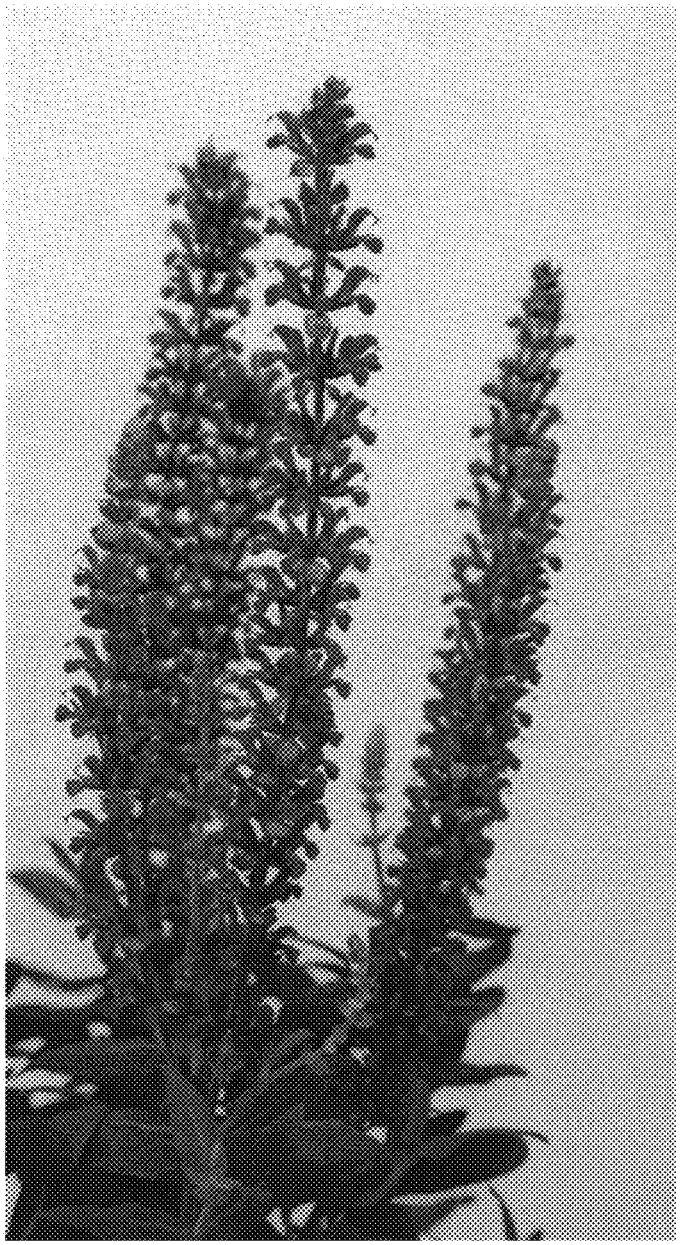
FIG. 3 shows, as nearly true as it is reasonably possible to make the same in color illustrations of this type, the typical inflorescence of 'GRUSALRP'.

The following is a detailed botanical description of a new and distinct variety of *Salvia* known as 'GRUSALRP', based upon observations of 3 month old plants in 11 cm nursery containers, grown outdoors in Rockanje, the Netherlands. Plants were grown using conventional field production protocols for *Salvia* plants which consisted of regular overhead irrigation. No pest or disease control measures were utilized in production. Temperatures ranged between 18 to 35 degrees Celsius during the day and 12 to 22 degrees Celsius at night. Plants were produced with full sun exposure and no photoperiodic treatments or artificial light was given to the plants. Observation data was recorded in September of 2019.

Those skilled in the art will appreciate that certain characteristics will vary with older or, conversely, with younger plants. 'GRUSALRP' has not been observed under all possible environmental conditions. Where dimensions, sizes, colors and other characteristics are given, it is to be understood that such measurements are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, 2015 edition.

A botanical description of 'GRUSALRP' and comparisons with the parent plants and most similar variety of common knowledge are provided below.

General plant description:

*Growth habit*.—A broad, upright herbaceous perennial.

*Plant profile*.—Broad, inverted triangular.

*Height*.—18.5 cm to the top of the foliar plane; 35.2 cm to the top of the floral plane.

*Spread*.—31.5 cm.

*Plant vigor*.—Moderate vigorous.

*Growth rate*.—Moderately fast growing.

*Propagation*.—Softwood stem cuttings; rooting is initiated in approximately 10 days when grown in a greenhouse with an ambient average temperature of 18 degrees Celsius.

*Time to produce a finished plant*.—Approximately 12 weeks are required to produce a marketable finished plant in a 13 cm pot.

*Pest resistance and susceptibility*.—Not any more or less tolerant or susceptible to pests or diseases known to effect *Salvia*.

*Environmental tolerances*.—Adapt to, at least, USDA Zones 3 to 10 and temperatures ranging from minus 28 degrees Celsius to 40 degrees Celsius; moderate to high tolerance to rain; moderate tolerance to wind.

Root system: Thin, fibrous, and freely branched.

Stem:

*Branching habit*.—Basally branching main stems growing from a caudex; freely branching with short lateral branches. Stems and branches emit a slight fragrance when touched, typical for the species. Pinching isn't required but will improve branching.

*Number of main stems per plant*.—8.

*Number of lateral branches per plant*.—4.

*Appearance and shape*.—Quandrangulate.

*Main stem length*.—13.5 cm, excluding the inflorescence.

*Main stem diameter*.—3.0 cm.

*Internode length*.—3.1 cm.

*Texture*.—Moderately pubescent; very short, soft hairs with an average length of 0.05 cm and colored translucent white, RHS NN155D.

*Luster*.—Matte.

*Aspect*.—Main stems are upright; lateral branches are at an average angle of 50 degrees to the main stems (varying between 10 and 90 degrees).

*Strength*.—Strong.

*Color, juvenile*.—Yellow-green, nearest RHS 144B.

*Color, mature*.—Yellow-green, nearest RHS 144B.

*Color at internodes*.—Yellow-green, nearest to RHS 145A.

Foliage:

*Arrangement*.—Opposite.

*Attachment*.—Petiolate.

*Division*.—Simple.

*Abundance of foliage*.—Abundant.

*Lamina*.—Dimensions — 7.0 cm long and 3.0 cm wide, on average. Shape — Narrow ovate to narrow oblong. Aspect — Flat to involute and slightly reflexed. Apex — Broad, bluntly acute. Base — Cordate. Margin — Crenate; not undulated. Pubescence and luster of adaxial surface — Smooth, glabrous, and very slightly glossy. Pubescence and luster of abaxial surface — Smooth, glabrous, and matte. Color — Juvenile foliage, adaxial surface — Green, nearest to RHS NN137B. Juvenile foliage, abaxial surface — Green, nearest to RHS 138B. Mature foliage, adaxial surface — Green, nearest to RHS NN137A. Mature foliage, abaxial surface — Yellow-green, nearest to RHS 147B. Venation — Pattern — Pinnate. Venation color, adaxial surface — Yellow-green, nearest to 145A. Venation color, abaxial surface — Yellow-green, RHS 145B.

*Petiole*.—Length — 0.8 cm. Width — Petioles are flattened; 0.225 cm, horizontally, and 0.125 cm, vertically. Texture, adaxial surface — Glabrous. Texture, abaxial surface — Glabrous. Margins — Moderately pubescent with short hairs with an average length of 0.01 cm and colored translucent white, nearest to RHS NN155D. Luster, adaxial surface — Slightly glossy. Luster, abaxial surface — Slightly glossy. Color, adaxial surface — Yellow-green, nearest to RHS 144A. Color, abaxial surface — Yellow-green, nearest to RHS 144B. Strength — Strong.

Inflorescence:

*Type*.—Terminal verticillaster with individual flowers in whorls.

*Natural flowering season*.—Late spring into summer in Rockanje, the Netherlands.

*Time to flower*.—Approximately 10 weeks after flowering.

*Flowering habit*.—Very freely flowering.

*Dimensions*.—An average of 19.1 cm high, not including peduncle, and 2.4 cm in diameter.

*Quantity of inflorescence per plant*.—15, on average.

*Quantity of flowers per inflorescence*.—Approximately 2,500 flowers and buds.

*Attitude*.—Upright.

*Peduncles*.—Length — 18.6 cm. Diameter — 0.2 cm. Aspect — Quadrangulate. Attitude — Upright; near vertical. Strength — Strong. Texture — Moderately pubescent; short glandular hairs with an average length of 0.05 cm and colored translucent white, nearest to RHS NN155D. Luster — Matte. Color — Green, RHS 1388, and moderately blotched greyed-purple, RHS 187A.

Flower buds:

*Shape*.—Obovate.

*Length*.—Average of 0.55 cm.

*Diameter*.—0.2 cm, horizontally; 0.3 cm, vertically.

*Texture*.—Moderately pubescent; very short glandular hairs with an average length of 0.02 cm and colored white, nearest to RHS NN155D.

*Luster*.—Matte.

*Color*.—Yellow-green, RHS 147A, and fading lighter towards the base, RHS 144B; veined purple, RHS N77C. Immature sepals are violet, RHS 86A, and finely dotted white, RHS NN155D.

Flower:

*Flowering habit*.—Freely flowering.

*Shape*.—Labiate.

*Dimensions of the flower height*.—Length is 1.05 cm, vertical height is 1.0 cm, and the horizontal width is 0.6 cm.

*Floral throat diameter*.—0.1 cm.

*Dimensions of the floral tube*.—Tube flattened; length is 0.45 cm, vertical height is 0.15 cm, and the horizontal width is 0.1 cm.

*Attitude*.—Outward facing.

*Fragrance*.—Non-fragrant.

*Lastingness*.—Approximately 10 days.

*Persistent*.—Self-cleaning.

*Pedicels*.—Dimensions — 0.2 cm long and 0.5 cm in diameter. Attitude — Upward; approximately 60 degrees to the peduncle axis. Strength — Moderately strong. Texture — Densely pubescent; short glandular hairs with an average length of 0.02 cm and colored translucent white, nearest to RHS NN155D. Luster — Matte. Color — Purple, nearest to in between RHS N77C and N77D.

*Petals*.—Quantity of Petals — 2. Arrangement — Labiate; one upper lip and one lower lip which with approximately 35 percent of the proximal portion of the corolla fused. Shape of petal lobes — Upper lip is folded into an oblanceolate shape; lower lip is spatulate with a larger central lobe and two smaller lateral lobes. Dimensions, free portion of the upper petal — 0.7 cm long and 0.1 cm wide. Dimensions, free portion of the lower petal — 0.6 cm long and 0.6 cm wide. Apex — Upper lip is emarginate; lobes of the lower lip are obtuse. Base — Truncate; fused at the base. Margin — Both petal lobes with entire margins; upper petal not undulated and lower petal slightly undulated. Aspect, upper lip — Concave. Aspect, lower lip — Central lobe is carinate and reflexed; lateral lobes are concave. Pubescence, texture and luster of upper surface — Both petals are glabrous, slightly velvety and matte. Pubescence, texture and luster of lower surface — Moderately pubescent with short glandular hairs that have an average length of 0.02 cm and are colored the same as the petal; slightly velvety and matte. Petal color when opening, upper surface — Upper petal — Violet, RHS N88B; no visible venation. Lower petal — Violet, RHS N89D; no visible venation. Petal color when opening, lower surface — Upper petal — Violet, RHS N88B, and finely dotted white, RHS NN155D; no visible venation. Lower petal — Violet, RHS N88A; no visible venation. Petal color when fully opened, upper surface — Upper petal — Violet, RHS N88B; no visible venation. Lower petal — Violet, RHS N88B; no visible venation. Petal color when fully opened, lower surface — Upper petal — Violet, RHS N88B, and finely dotted white, RHS NN155D; no visible venation. Lower petal — Violet, RHS N88A; no visible venation. Upper petal, faded color — Upper petal — Violet, RHS N88B; no visible venation. Lower petal — Central lobe is violet, RHS N88A; lateral lobes are violet, RHS 86B; no visible venation. Lower petal, faded color — Upper petal — Violet, RHS N88A, and finely dotted white, RHS NN155D; no visible venation. Lower petal — Central lobe is violet, RHS N88A; lateral lobes are violet, RHS 86B; no visible venation. Floral throat color — Violet, RHS 86B; no visible venation. Floral tube color when fully opened, inner and outer surfaces — Violet, RHS 86B, and fading to white towards the base, nearest to RHS N155A; no visible venation.

*Calyx*.—Shape — Campanulate. Dimensions — Calyx is flattened; length is 0.6 cm, the height is 0.35 cm, and the width is 0.25 cm. Sepals — Length — 0.6 cm. Width — 0.25 cm. Arrangement — Campanulate; the proximal 70 percent of the sepals are fused. Quantity — 2. Shape — Both sepals oblanceolate. Apex — Upper sepal is emarginate; lower sepal is cleft. Base — Fused. Sepal lobe margin — Both sepals are entire; not undulated; moderately pubescent with very short glandular hairs with an average length of 0.2 cm and colored translucent white, nearest to RHS NN155D. Pubescence, texture and luster, upper surface — Both sepals are smooth, glabrous, and matte. Pubescence, texture and luster, lower surface — Both sepals are moderately pubescent with very short glandular hairs with an average length of 0.2 cm and colored white, nearest to RHS NN155D; matte. Color when opening, upper surface — Green, nearest to in between RHS 138B and 138C; veined darker green, RHS 139B. Color when opening, lower surface — Yellow-green, RHS 147A, and fading lighter towards the base, RHS 144B; veined purple, RHS N77C. Color when fully opened, upper surface — Green, nearest to in between RHS 138B and 138C; veined darker green, RHS 139B. Color when fully opened, lower surface — Yellow-green, RHS 147B, and fading lighter towards the base, RHS 147C; veined purple, RHS N77C. Floral bract — Position — Below each floral bud. Quantity — 1. Shape — Broad ovate. Length — 0.7 cm. Width — 0.6 cm. Apex — Abruptly acute. Base — Broad cuneate. Margin — Entire. Pubescence, texture and luster, upper surface — Smooth, glabrous, and matte. Pubescence, texture and luster, lower surface — Smooth, glabrous, and matte. Color when fully opened, upper surface — Yellow-green, RHS 145D, and slightly suffused with greyed-purple, RNS 186D; veined green, RHS 137C. Color when fully opened, lower surface — Yellow-green, RHS 145D, and slightly suffused with greyed-purple, RNS 186D; veined green, RHS 137C.

Reproductive organs:

*Stamens*.—Quantity — 2. Anthers — Attachment — Basifixed. Shape — Narrow oblong. Dimensions — Approximately 0.15 cm long and 0.05 cm wide. Color — Black, nearest to RHS 203A. Filaments — Length — 0.4 cm, on average. Color — Violet, RHS N87D. Pollen, amount — Sparse. Pollen color — Greyed-yellow, nearest to RHS 160B.

*Pistil*.—Quantity — 1. Length — 1.4 cm. Style — Length — 1.3 cm. Color — Violet-blue, RHS 90D, and fading to white towards the base, RHS N155A. Stigma — Shape — Cleft; decurrent. Length — 0.1 cm. Diameter — 0.1 cm. Color — Violet-blue, RHS N89B. Ovary Color — Yellow-green, RHS 144A.

Seed and fruit: No fruit or seeds have been detected to date.

COMPARISONS WITH THE PARENT PLANTS AND MOST SIMILAR VARIETY OF COMMON KNOWLEDGE

Plants of the new cultivar 'GRUSALRP' differ from its parent, *Salvia* x *sylvestris* 'Rianne' (Community Plant Variety Rights grant number 41746), by the characteristics described in Table 1.

TABLE 1

| Characteristic | 'GRUSALRP' | 'Rianne' |
|---|---|---|
| Plant height. | Taller than 'Rianne'. | Shorter than 'GRUSALRP'. |
| Foliage size. | Larger than 'Rianne'. | Smaller than 'GRUSALRP'. |
| Flower size. | Larger than 'Rianne'. | Smaller than 'GRUSALRP'. |

Plants of the new cultivar 'GRUSALRP' may be distinguished from its most similar known commercial comparator, *Salvia* 'Blauhugel' (not protected), by the characteristics described in Table 2.

TABLE 2

| Characteristic | 'GRUSALRP' | 'Blauhugel' |
|---|---|---|
| Plant height, in flower. | Shorter than 'Blauhugel'. | Taller than 'GRUSALRP'. |
| General coloration of the flower. | Darker shad of violet. | Lighter shade of violet. |

That which is claimed is:

1. A new and distinct variety of *Salvia* hybrid plant named 'GRUSALRP', substantially as described and illustrated herein.

* * * * *